(12) United States Patent
Andarawis et al.

(10) Patent No.: US 8,339,149 B2
(45) Date of Patent: Dec. 25, 2012

(54) SYSTEMS FOR INSPECTION OF SHROUDS

(75) Inventors: Emad Andarawis Andarawis, Ballston Lake, NY (US); Chukwueloka Obiora Umeh, Hamilton, OH (US)

(73) Assignee: General Electric Company, Niskayuna, NY (US)

( * ) Notice: Subject to any disclaimer, the term of this patent is extended or adjusted under 35 U.S.C. 154(b) by 261 days.

(21) Appl. No.: 12/871,472

(22) Filed: Aug. 30, 2010

(65) Prior Publication Data

US 2010/0321048 A1  Dec. 23, 2010

Related U.S. Application Data

(62) Division of application No. 12/054,565, filed on Mar. 25, 2008, now Pat. No. 7,852,092.

(51) Int. Cl.
*G01R 27/26* (2006.01)
(52) U.S. Cl. ........................................ 324/699; 324/658
(58) Field of Classification Search .................. 324/658, 324/699
See application file for complete search history.

(56) References Cited

U.S. PATENT DOCUMENTS

| | | | |
|---|---|---|---|
| 3,141,651 | A | 7/1964 | Moyer |
| 5,127,793 | A | 7/1992 | Walker et al. |
| 6,644,917 | B2 | 11/2003 | Zhao et al. |
| 6,692,222 | B2 | 2/2004 | Tsuru et al. |
| 7,180,305 | B2 | 2/2007 | Andarawis et al. |
| 7,215,129 | B1 | 5/2007 | Andarawis et al. |
| 7,271,894 | B2 | 9/2007 | Devitt et al. |
| 7,332,915 | B2 | 2/2008 | Andarawis et al. |
| 7,333,913 | B2 | 2/2008 | Andarawis et al. |
| 2006/0132147 | A1 | 6/2006 | Balasubramaniam et al. |
| 2006/0239813 | A1 | 10/2006 | Shah et al. |
| 2007/0128016 | A1 | 6/2007 | Dasgupta et al. |
| 2007/0222459 | A1 | 9/2007 | Andarawis et al. |
| 2008/0072681 | A1 | 3/2008 | Ruud et al. |
| 2008/0156773 | A1* | 7/2008 | Kitade et al. .................... 216/84 |
| 2009/0003991 | A1 | 1/2009 | Andarawis et al. |

* cited by examiner

*Primary Examiner* — Vincent Q Nguyen
(74) *Attorney, Agent, or Firm* — Penny A. Clarke

(57) ABSTRACT

A system to measure thickness of a shroud is provided. The system includes at least one resistive element embedded within the shroud. The system also includes an impedance measurement device that measures a total resistance associated with the at least one resistive element.

6 Claims, 5 Drawing Sheets

US 8,339,149 B2

SYSTEMS FOR INSPECTION OF SHROUDS

BACKGROUND

The invention relates generally to systems and methods for assessing wear or damage to turbine parts and more specifically, to wear in a shroud of the turbine.

There are several techniques that are currently used for inspection of turbine parts. A commonly used technique includes schedule-based shutting down of a turbine and physically examining parts at predetermined intervals. However, the process is inefficient, time consuming, and costly due to turbine shut down and maintenance. Further, several on-line methods have been developed for detecting wear-out of turbine parts such as, but not limited to, shrouds.

For example, Blatchley and coworkers (C. C. Blatchley and R. J. Bricault Jr., in Tribological Mechanisms & Wear Problems in Materials, ASM International, Metals Park, Ohio, 1987, pp. 95-100 and C. C. Blatchley and P. G. Loges, in Advances in Steam Turbine Technology for Power Generation, ASME, New York, N.Y., 1990, Vol. 10, pp. 9-13) developed a "surface layer activation" technique to monitor wear and corrosion in steam turbines by detecting gamma-ray signals from radionuclides imbedded in trace amounts in surfaces of wearing parts. The nuclides served as surface markers, and were produced by controlled exposure to particles from Van de Graaff or cyclotron accelerators.

However, the above techniques can only be applied to steam turbines, which are closed systems, so that radioactive materials in the water stream will not be released to the environment. The technique cannot be applied to gas turbines because the exhaust is released into the air, and radioactive elements will be detrimental to the environment. Also, a gas sampling and analysis system would be needed in the area of the exhaust stream if one decided to use this technique on gas turbine engines. This technique further finds challenges in aircraft engine systems where the sampling and analysis system needs to occur online or during flight, thus increasing the complexity.

There are other existing coating life estimation methods that are typically based on average effects of stress and temperature profiles of the parts. Such methods are unable to focus on individual parts since they do not take into account conditions that the parts installed in a particular turbine actually encounter, such as, but not limited to, foreign object damage, variation of operating conditions from site to site, and occasional overfiring of the turbine. All of the conditions can drastically influence the true remaining life of the individual parts. Blade rubs also contribute to conditions where a small portion of the shroud may experience more localized damage than the rest of the shroud.

Thus, there exists a need for an on-line assessment of wear of gas turbine parts that addresses one or more aforementioned issues. In applications that utilize a clearance control system, since clearance measurements typically measure the distance between the installed sensor and the blades and assesses the blade to shroud clearance based on the expected shroud thickness, accurate assessment of the extent of shroud wear is necessary to maintain the clearance measurement accuracy of the system.

BRIEF DESCRIPTION

In accordance with an embodiment of the invention, a system to measure thickness of a shroud is provided. The system includes at least one resistive element embedded within the shroud. The system also includes an impedance measurement device configured to measure a total resistance associated with the at least one resistive element.

In accordance with another embodiment of the invention, a system for measuring thickness of a shroud is provided. The system includes an electronic circuit embedded within the shroud. The electronic circuit includes an inductor and a capacitor coupled to the inductor, such that a capacitance of the capacitor is a function of a wear of the shroud.

In accordance with another embodiment of the invention, a system for measuring thickness of a shroud is provided. The system includes an electronic circuit embedded within the thermal barrier coating and the abradable coating layer. The electronic circuit includes an inductor and a capacitor coupled to the inductor. The thermal barrier coating and the abradable coating serve as a magnetic material forming the core of the inductor, such that a inductance of the inductor is a function of a wear of the shroud.

In accordance with another embodiment of the invention, a system for measuring thickness of a shroud is provided. The system includes a bulk electrode embedded within the shroud, wherein a reduction in a cross-sectional area of the electrode due to wearing out of the shroud results in a change in a resistance of the electrode. The system also includes an impedance measurement device configured to measure the resistance of the bulk electrode.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the invention include systems and methods for inspection of a shroud. Embodiments of the invention disclosed herein, assess wear on the shroud by measuring thickness of the shroud. More specifically, a change in resistance of one or more resistive elements embedded within the shroud is measured, which occurs due to wearing out of the shrouds. The wearing of the shroud may occur due to various reasons. A non-limiting example includes wearing away of the shroud due to rubs that occur between a tip of a turbine blade and the shroud.

Figure 1:
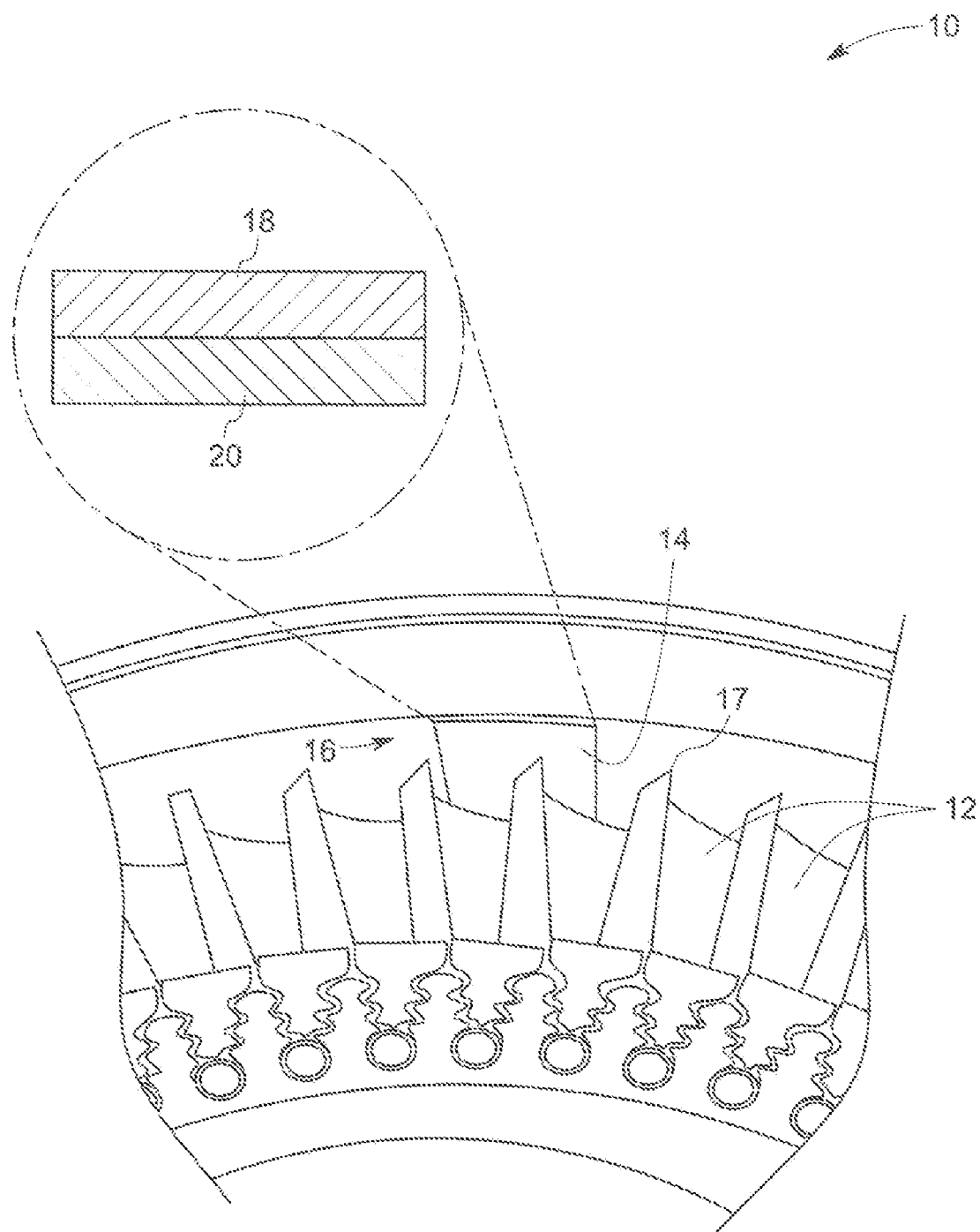
FIG. 1 is a schematic illustration of a typical turbine blade system including multiple blades and a shroud.

FIG. 1 is a schematic illustration of a typical turbine blade system 10 including multiple blades 12 and a shroud 14 separated by a clearance 16. A reduction of the clearance 16 may result in rubbing of a tip 17 of the blades 12 against the shroud 14. Such an interaction may be tolerated by providing an abradable coating layer 18 deposited upon a thermal barrier coating layer 20. The abradable coating layer 18 is designed to release fine wear debris when machined by the blades 12 rotating at a high velocity, while causing minimal wear of the blades 12.

Figure 2:
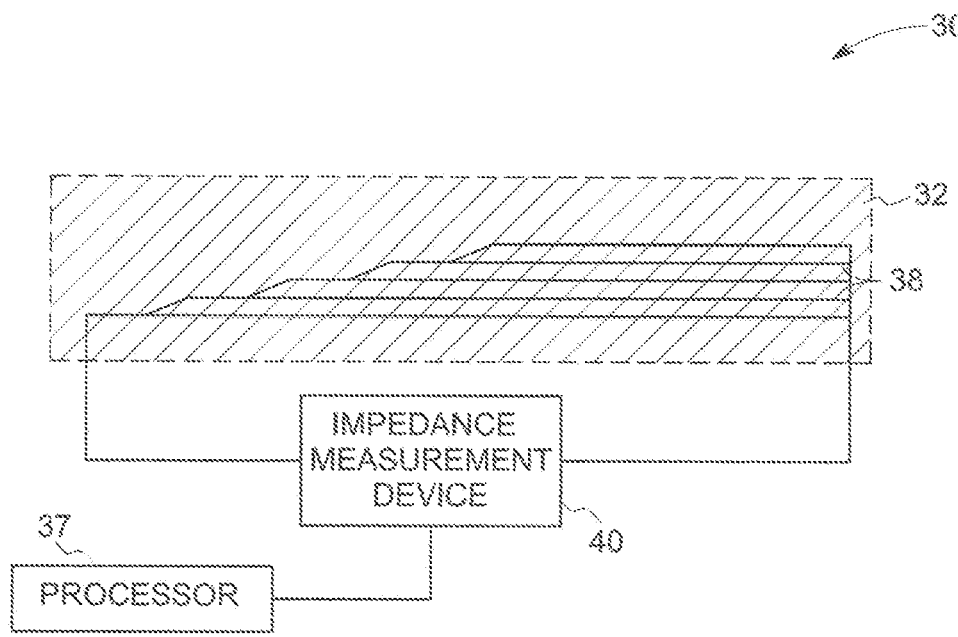
FIG. 2 is a schematic cross-sectional view of a system for measuring thickness of the shroud in FIG. 1, in accordance with embodiments of the invention.

FIG. 2 is a schematic cross-sectional view of a system 30 for measuring thickness of the shroud 14 in FIG. 1. In the illustrated embodiment, a combination of a thermal barrier coating layer and an abradable coating layer 32 is deposited on a base portion of the shroud 14. In a particular embodiment, the thermal bather coating layer 32 has a thickness of about 0.005 inch to about 0.1 inch. In an exemplary embodiment, the abradable coating layer has a thickness of about 0.005 inch to about 0.1 inch. The system 30 includes at least one resistive element 38 that is embedded within the barrier and abradable coating layers 32. It should be noted that in absence of the thermal barrier coating layer and the abradable coating layer, the resistive element 38 is embedded within the shroud. In a particular embodiment, the at least one resistive element 38 is embedded within the thermal barrier coating and the abradable coating layers via a deposition process such as, but not limited to, a direct write printing process, an ink jet process or a decal process. In a particular embodiment, each of the at least one resistive element 18 comprises a single material. In another embodiment, the resistive element comprises multiple geometries resulting in different resistivities. In yet another embodiment, each of the at least one resistive element 38 comprises multiple materials having different resistivities. Non-limiting examples of the materials used are platinum, platinum-rhodium, platinum-iridium, nickel, or tungsten with appropriate oxidization protection. In yet another embodiment, the resistive element 38 is deposited directly into a shroud material. An impedance measurement device 40 measures a total resistance associated with the at least one resistive element 38. In one embodiment, the impedance is measured by applying a known current, and measuring the voltage drop across the resistive element 38. In another embodiment, a known voltage is applied, and the associated current is measured to determine the resistance of the resistive element 38. A processor 37 is optionally coupled to the impedance measurement device 40 and is configured to convert the resistance to a shroud thickness value.

Figure 4:
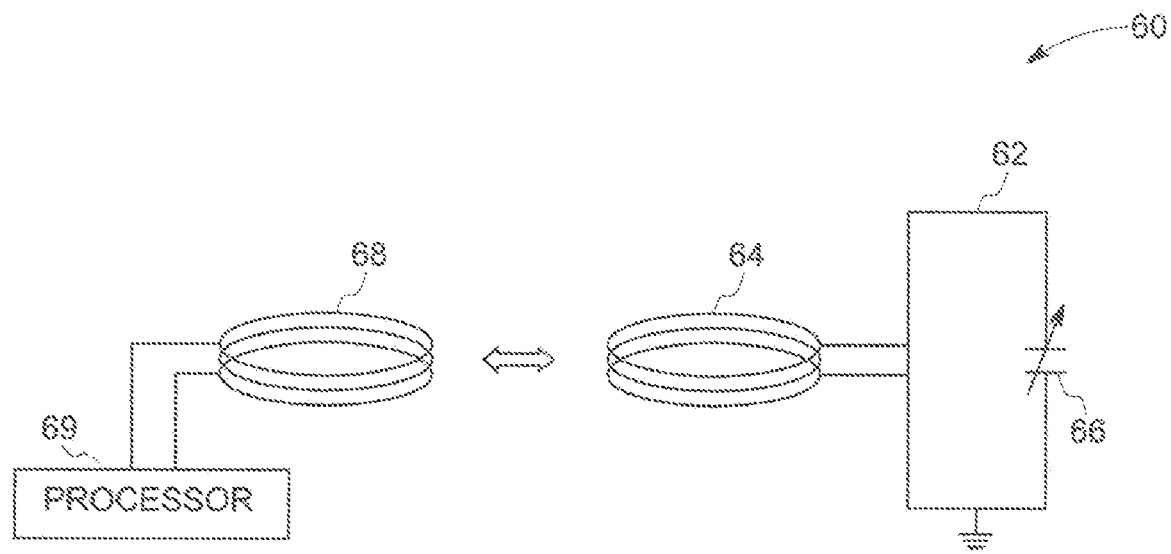
FIG. 4 is a schematic representation of another exemplary system including a LC circuit, to measure thickness of a shroud in accordance with embodiments of the invention.

For the example embodiment illustrated by FIGS. 2 and 4, the at least one resistive element 38 includes multiple wires R1, R2 . . . R5. For this configuration, a break in at least one of the wires due to a wear in the shroud corresponds to a change in a total resistance of the wires, such that the impedance measurement device measures a stepwise increase in resistance due to the wear on the shroud. It should be noted that the 5 wires shown in FIG. 2 are merely illustrative and other numbers of wires can be employed. According to a particular embodiment, at least a subset of the wires are equipped with at least two contact points to measure the resistance, such that the total resistance comprises an equivalent resistance in a parallel connection of the wires.

Figure 3:
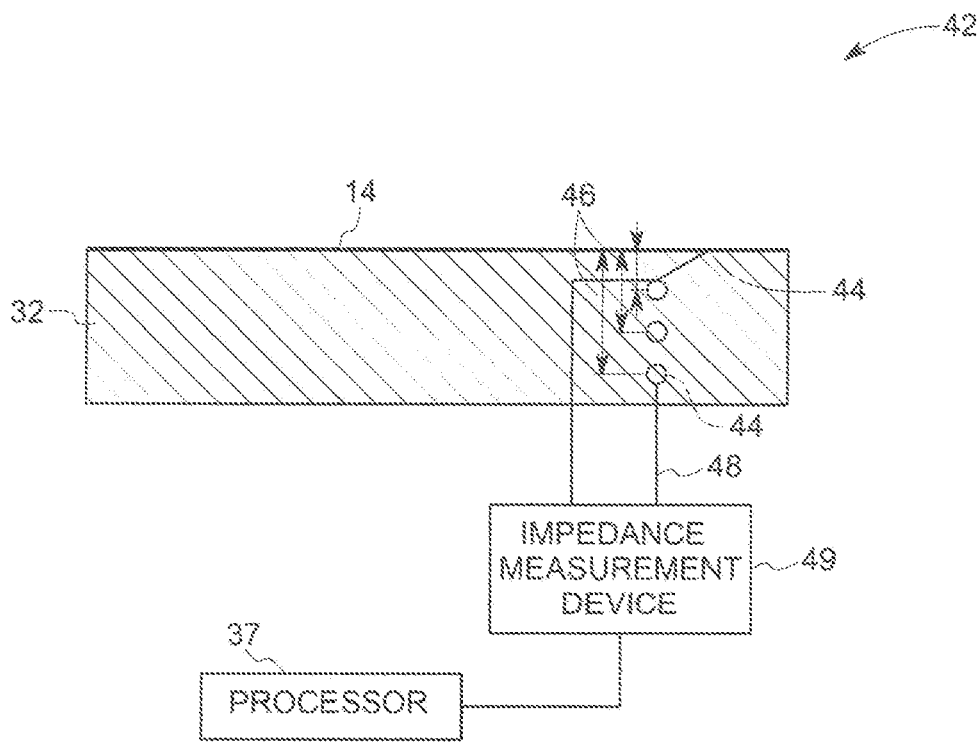
FIG. 3 is a schematic illustration of an exemplary measurement system including multiple wires embedded at different radial depths at a given position on a circumference of the shroud in FIG. 1, in accordance with embodiments of the invention.

For the example arrangement depicted in FIG. 3, multiple resistive elements 38 are embedded at different locations around a circumference of the shroud. In a non-limiting example, the different locations are spaced at about 10 degrees apart circumferentially. For the exemplary arrangement shown in FIG. 3, the resistive elements 38 are multiple wires that are embedded at different radial depths, such that at least a subset of the wires are arranged at different radial positions at a given position along the circumference of the shroud. In one embodiment, the resistance of the wires embedded at different depths is the same. In another embodiment, the resistance of the wires at the different depths are different. This enables calibration of the measurements relative to temperature. In one embodiment, each of the wires has a diameter in a range between about 1 mil to about 20 mil, depending on the process used to deposit the wires.

In another exemplary embodiment, each of the at least one resistive element 38 comprises a bulk resistive element, wherein a wear in the shroud corresponds to a change in a resistance of the bulk resistive element. For certain embodiments, the bulk resistive element(s) comprises a single material. For other embodiments, the bulk resistive element(s) comprises multiple materials with different resistivities.

FIG. 3 is a schematic illustration of an exemplary measurement system 42. The system 42 includes multiple wires 44 embedded at different radial depths 46 at a given position 48 on a circumference of the shroud 14. In the illustrated example, the system 42 includes five wires. As noted above, the example arrangement of five wires is illustrative and is non-limiting. An impedance measurement device 49 measures a total resistance associated with the wires 44. In a particular embodiment, the resistance of the wires 44 embedded at the different depths 46 is the same. In another embodiment, the resistance of the wires 44 embedded at different depths 46 is different. This latter arrangement can be accomplished, for example, by using wires formed of different materials and/or using wires having different geometries and/or dimensions.

FIG. 4 is a schematic illustration of another exemplary system 60 to measure thickness of a shroud 14, as referenced in FIG. 1. The system 60 includes an electronic circuit 62 embedded within a thermal barrier coating layer and an abradable coating layer (not shown). It should be noted that in absence of the thermal barrier coating layer and the abradable coating layer, the electronic circuit 62 is embedded within the shroud 14. The electronic circuit 62 includes an inductor 64 that is coupled to a capacitor 66. The capacitor 66 is formed such that the thermal barrier coating and the abradable coating layer serve as a dielectric material of the capacitor, wherein a capacitance of the capacitor 66 is a function of a wear of the shroud. In a case where there is no thermal barrier coating, the abradable coating and/or the shroud material will serve as a dielectric material of the capacitor. In another embodiment, an explicit high temperature dielectric material such as, for example, alumina can be used as the dielectric material of the capacitor 66. For the example arrangement depicted in FIG. 5, the capacitor 66 comprises a capacitive comb deposited between the thermal barrier coating layer and the abradable layer. For the arrangement shown in FIG. 4, a remote reader 68 measures a resonance frequency of the electronic circuit 62. In a particular embodiment, the remote reader comprises a coil deposited outside of the shroud. The system 60 optionally includes a processor 69 that is configured to receive the data from the remote reader 68 and to convert the data to a shroud thickness value. In another exemplary embodiment, the thermal barrier coating and the abradable coating serve as a magnetic material forming the core of the inductor 64, such that an inductance of the inductor 64 is a function of a wear of the shroud.

Figure 5:
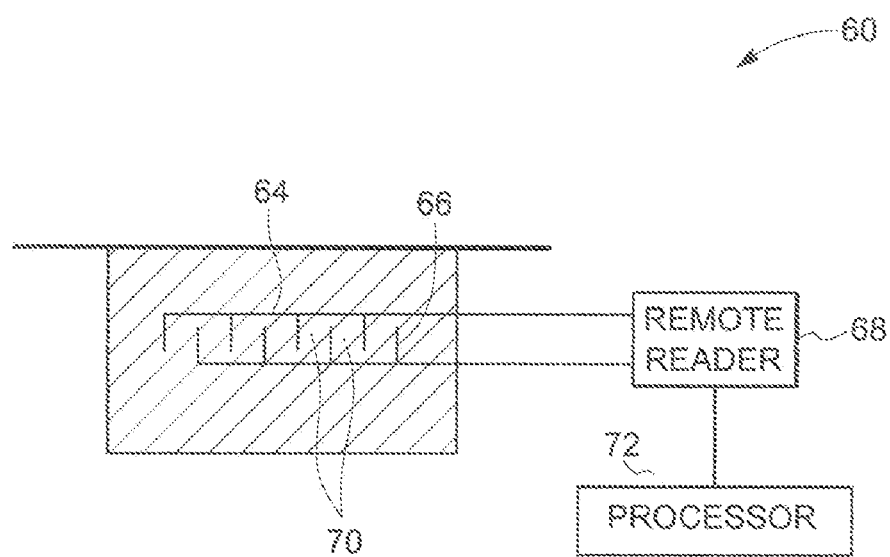
FIG. 5 is a schematic of a cross-sectional view of an exemplary implementation of the system in FIG. 4.

FIG. 5 is a schematic of a top view of a physical structure of the system 60 in FIG. 4. In the illustrated embodiment, the capacitor 66 is a comb structure with a thermal barrier coating layer and abradable coating layer 64 forming a dielectric between wires 70. It should be noted that in absence of the thermal barrier coating layer and the abradable coating layer, the electronic circuit 62 is embedded within the shroud 14. In another nonlimiting example, the capacitor 66 comprises a parallel plate capacitor with the TBC and abradable layers serving as the dielectric material. In all of these examples, a wear in the shroud 14 leads to wearing out of the dielectric, consequently resulting in a change in capacitance. The remote reader 68 measures a transient frequency that is a function of the capacitance.

Figure 6:
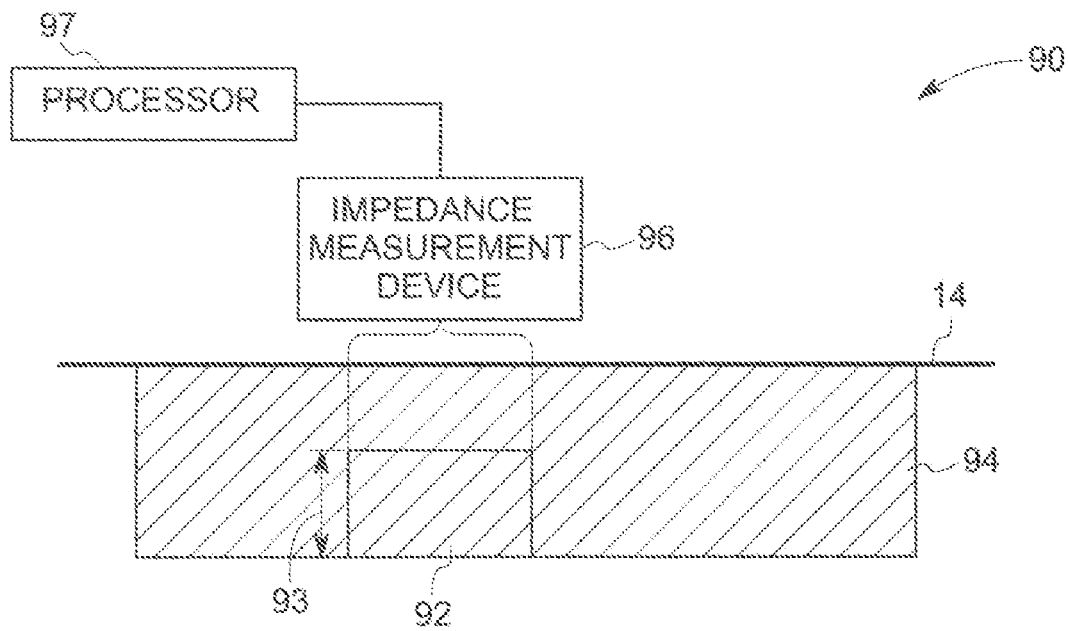
FIG. 6 is a schematic illustration of another exemplary system including a bulk electrode, to measure thickness of a shroud in accordance with embodiments of the invention.

FIG. 6 is a schematic illustration of another exemplary system 90 to measure thickness of a shroud. The system 90 includes a bulk electrode 92 of length referenced by numeral 93 embedded within a thermal barrier coating layer and an abradable coating layer 94, or directly in a shroud material wherein a reduction in a cross-sectional area of the electrode 92 due to wearing out of the shroud results in a change in a resistance of the electrode 92. It should be noted that in absence of the thermal barrier coating layer and the abradable coating layer, the bulk electrode 92 is embedded within the shroud 14. Non-limiting examples of a material used in the electrode include platinum, platinum-rhodium, platinum-iridium, nickel, or tungsten with appropriate oxidization protection. An impedance measurement device 96 measures resistance of the bulk electrode 92. A processor 97 is optionally coupled to the impedance measurement device 96 and is configured to receive data from the electrode(s). In one embodiment, the impedance is measured by applying a known current, and measuring the voltage drop across the bulk electrode 92. In another embodiment, a known voltage is applied, and the associated current is measured to determine the resistance of the bulk electrode 92.

Figure 7:
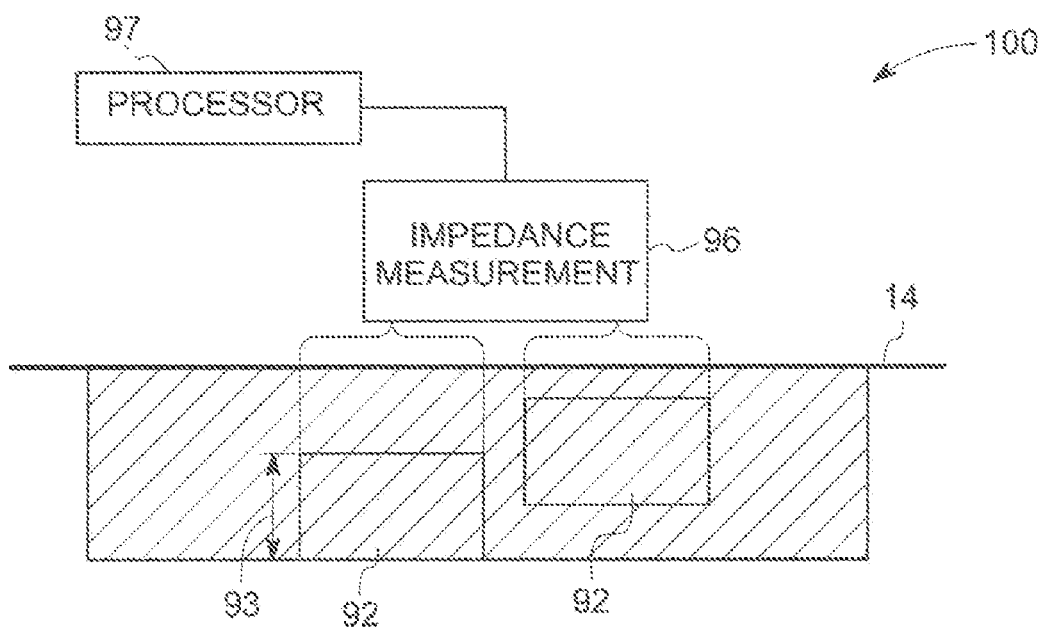
FIG. 7 is a schematic illustration of another exemplary system including a bulk electrode and a reference electrode, to measure thickness of a shroud in accordance with embodiments of the invention.

FIG. 7 is a schematic illustration of yet another exemplary measurement system 100, which is similar to the system 90 discussed above with reference to FIG. 6 but further includes a reference electrode 102. The reference electrode 102 is deposited at a depth in the shroud 14 such that a resistance of the reference electrode changes only as a result of a change in environmental factors such as, but not limited to, temperature and pressure. Namely, the reference electrode is deposited well below the surface of the abradable and TBC coatings, (or bare shroud surface if a TBC coat is not deposited on the shroud) such that the reference electrode is not subject to wear during rotation of turbine blades. Accordingly, the reference electrode 102 enables calibration of the impedance measurement of the electrode 92 in FIG. 5. As indicated, an impedance measurement device 96 compares a change in resistance in electrode 92 that is affected by a wear in the shroud 14 in addition to the change in environmental conditions, with a change in resistance of the reference electrode 102, which is only affected by the change in environmental conditions.

Figure 8:
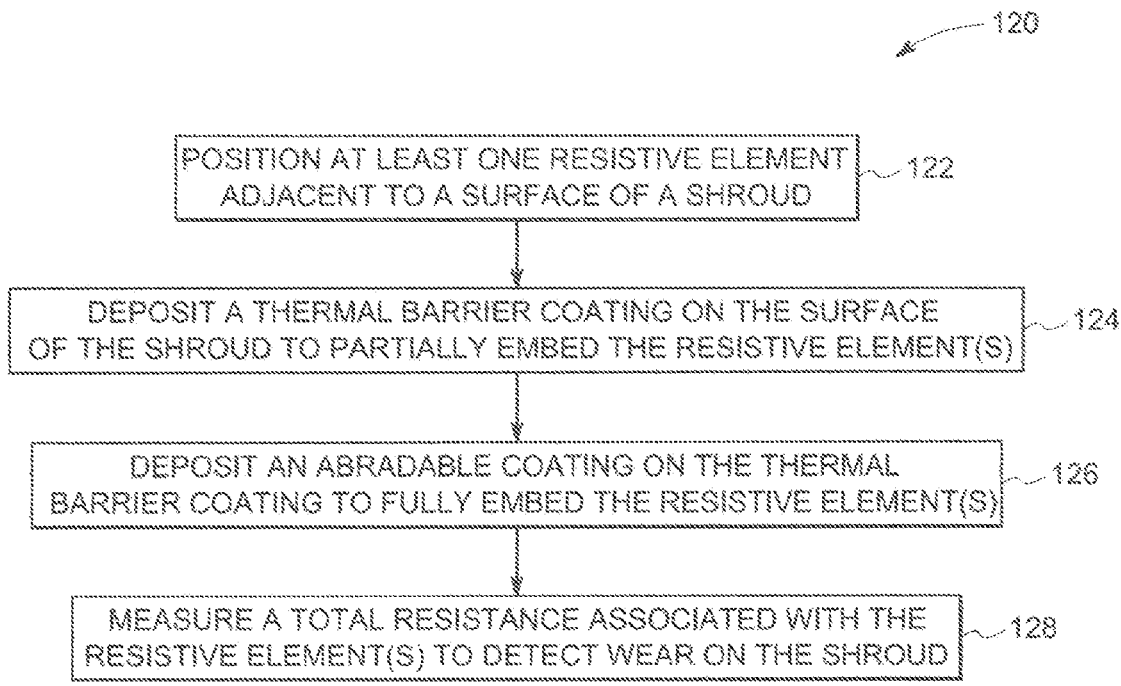
FIG. 8 is a flow chart representing steps in an exemplary method for measuring thickness of a shroud.

FIG. 8 is a flow chart representing steps in an exemplary method 120 for measuring thickness of a shroud. The method 120 includes positioning at least one resistive element adjacent to a surface of a shroud in step 122. A thermal barrier coating is deposited in step 124 on the surface of the shroud to partially embed the at least one resistive element. An abradable coating is further deposited on the thermal barrier coating in step 126 to fully embed the at least one resistive element. If a TBC coating is not used, the element can be built directly into a shroud material. A total resistance associated with the at least one resistive element is measured in step 128 to detect a wear on the shroud.

Figure 9:
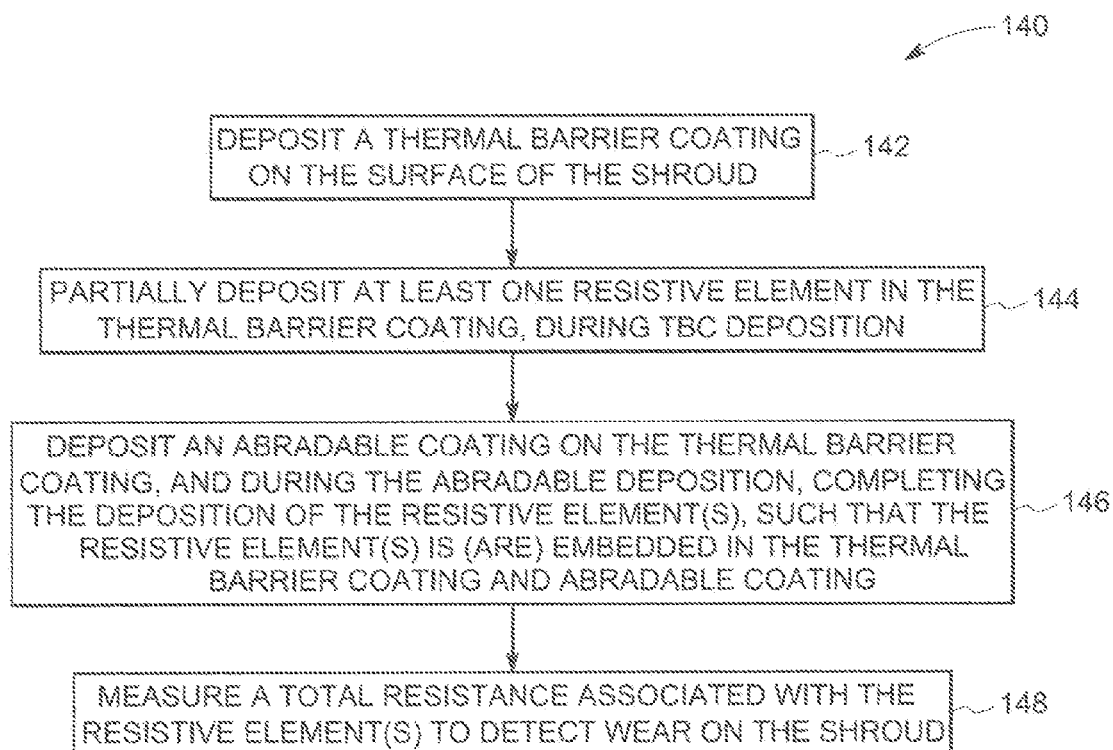
FIG. 9 is a flow chart representing steps in another exemplary method for measuring thickness of a shroud.

FIG. 9 is a flow chart representing another exemplary method 140 for measuring thickness of a shroud. The method 140 includes depositing a thermal barrier coating on a surface of the shroud in step 142. At least one resistive element is partially deposited during the deposition of the thermal barrier coating in step 144. An abradable coating is deposited on the thermal barrier coating in step 146 and deposition of the at least one resistive element is simultaneously completed such that the at least one resistive element is embedded in the thermal barrier coating and the abradable coating. In a particular embodiment, the resistive element (s) is/are deposited via a direct write process. In another embodiment, the resistive element (s) is/are deposited via an ink-jet process. In yet another embodiment, the resistive element (s) is/are deposited via a decal process. In another embodiment, the resistive element(s) are built directly into the shroud material with several of the manufacturing methods available. A total resistance associated with the at least one resistive element is measured in step 148 to detect a wear on the shroud.

The various embodiments of systems and methods for inspection of shrouds described above thus provide an online assessment of wear—in a shroud in a turbine engine. Additionally, the techniques and systems may be used in engines outfitted with a clearance sensor and/or having an active clearance control system. In addition, the present techniques enable accurate blade to shroud clearance measurement in presence of a shroud wear. Further, the techniques enable localization of rubs in the shroud occurring due to the blades, thus reducing clearance added to compensate for out of roundness. These techniques and systems also allow for improved turbine prognosis and field inspection techniques.

Of course, it is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the use of an example of multiple bulk resistive elements described with respect to one embodiment can be adapted for use in a system employing resistive elements at various radial depths with different resistances described with respect to another. Similarly, the various features described, as well as other known equivalents for each feature, can be mixed and matched by one of ordinary skill in this art to construct additional systems and techniques in accordance with principles of this disclosure.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for measuring thickness of a shroud, the system comprising:
    an electronic circuit embedded within the shroud, the electronic circuit comprising: an inductor; and
    a capacitor coupled to the inductor, wherein a capacitance of the capacitor is a function of a wear of the shroud;
    the system further comprising a remote reader configured to measure a transient frequency of the circuit.

2. The system of claim 1, wherein the remote reader comprises a coil deposited outside of the shroud.

3. The system of claim 1, wherein the shroud comprises a thermal barrier coating deposited on a base portion of the shroud and an abradable coating layer deposited on the thermal barrier coating, wherein the electronic circuit is embedded within at least one of the thermal barrier coating and the abradable coating, and wherein the thermal barrier coating and the abradable coating serve as a dielectric material of the capacitor.

4. The system of claim 3, wherein the capacitor comprises a capacitive comb deposited between the thermal barrier coating layer and the abradable layer.

5. The system of claim 1, wherein the capacitor comprises a capacitive comb deposited directly into the shroud.

6. A system for measuring thickness of a shroud, the system comprising:
- an electronic circuit embedded within the shroud, the electronic circuit comprising:
- an inductor, wherein an inductance of the inductor is a function of a wear of the shroud; and
- a capacitor coupled to the inductor;
- the system further comprising a remote reader configured to measure a transient frequency of the circuit.

\* \* \* \* \*